US 6,723,960 B2

(12) United States Patent
DiMartino et al.

(10) Patent No.: US 6,723,960 B2
(45) Date of Patent: Apr. 20, 2004

(54) HEATER FOR ORTHOPEDIC SPLINTS

(76) Inventors: Arthur DiMartino, 95 Walker St., Weston, MA (US) 02493; William A. Johnson, 463 Hanlon Rd., Holliston, MA (US) 01746

( * ) Notice: Subject to any disclaimer, the term of this patent is extended or adjusted under 35 U.S.C. 154(b) by 55 days.

(21) Appl. No.: 10/101,604

(22) Filed: Mar. 21, 2002

(65) Prior Publication Data

US 2003/0178404 A1 Sep. 25, 2003

(51) Int. Cl.[7] .............................. H05B 3/36; H05B 3/34; F27D 11/02; F27D 19/00
(52) U.S. Cl. ....................................... 219/386; 219/494
(58) Field of Search .............................. 219/385, 386, 219/402, 404, 521, 412–414, 494

(56) References Cited

U.S. PATENT DOCUMENTS

| | | | |
|---|---|---|---|
| 1,498,655 A | * 6/1924 | Hauptman | 219/549 |
| 3,746,837 A | * 7/1973 | Frey et al. | 219/521 |
| 3,879,171 A | * 4/1975 | Tulis | 219/521 |
| 4,163,896 A | * 8/1979 | McAvinn et al. | 219/386 |
| 4,244,771 A | 1/1981 | Pierce | |
| 4,523,078 A | * 6/1985 | Lehmann | 219/386 |
| 4,677,970 A | 7/1987 | Green et al. | |
| 5,140,136 A | * 8/1992 | Fellows et al. | 219/521 |
| 5,615,604 A | 4/1997 | Chenglin | |
| 5,782,780 A | 7/1998 | Mason et al. | |
| 5,922,227 A | 7/1999 | McMurtrie | |
| 5,981,909 A | * 11/1999 | Freeman | 219/386 |
| 6,018,614 A | 1/2000 | Garcia et al. | |
| 6,072,158 A | 6/2000 | McNally | |
| 6,138,662 A | 10/2000 | Jones | |

* cited by examiner

Primary Examiner—Joseph Pelham
(74) Attorney, Agent, or Firm—Richard C. Litman

(57) ABSTRACT

A heater device for orthopedic splints is organized in a portable container to preheat plastic splint sheets for immediate use in forming various shapes to fit and to stabilize the injured body portion of the patient. The heater is incorporated in a container having heating elements, a temperature controller, a cut-out sensor, and a supply of plastic orthopedic splint sheets inside. A control panel outside contains a power-on indicator lamp, a heater-on indicator lamp, and a temperature dial control or a toggle switch having multiple preset temperature settings. An AC power input element is on one side of the container. A supply of plastic splint sheets are contained in a separate inner compartment.

11 Claims, 3 Drawing Sheets

HEATER FOR ORTHOPEDIC SPLINTS

BACKGROUND OF THE INVENTION

1. Field of the Invention

The present invention relates generally to heaters. More specifically, the invention is a portable electric heater in a carrying case for warming sheets of formable plastic material to form various contours of orthopedic splints.

2. Description of the Related Art

The related art of interest describes many portable heater devices, but none discloses the present invention. There is a need for having ready warmed and pliable plastic sheets for orthopedic splint use in emergencies or non-emergencies by a medic, physician, or a professional occupational therapist.

U.S. Pat. No. 5,922,227 issued on Jul. 13, 1999, to Dallas McMurtrie describes a portable low wattage electric heater having a compact housing with two removable heating panels mounted therein. The heater may be connected to different electrical power supplies having different voltages with a switch provided to connect one or the other of the two heating elements to the electrical power supply. An adjustable thermostat is provided to prevent overheating of the heating elements. The heating elements may be light bulbs to allow the heater to be used as a lamp.

U.S. Pat. No. 6,018,614 issued on Jan. 25, 2000, to Robert M. Garcia et al. describes a portable compressed air heater having a portable housing. The system includes a hot air distribution system for directing hot air to a substrate, a heater module for receiving and heating air, and equipped with an adjustable velocity element, an interface conduit connecting the heater module to a system controller, circuitry directed by the controller for operation of the heating module, an air-in port, an air-out port, a heater-power conduit, a temperature controller, an air pressure monitor, and an air pressure adjuster.

U.S. Pat. No. 6,072,158 issued on Jun. 6, 2000, to Douglas J. McNally describes a method and apparatus for heating a plastic sheet with an air diffuser plate.

U.S. Pat. No. 4,244,771 issued on Jan. 13, 1981, to Larry L. Pierce describes a thermoplastic sheet strip heater assembly comprising a heater housing including a heat development channel, with a heat escape flue defined in a bed of insulation, a sheet support surface located above the channel with a central opening aligned with the flue, a protective grid covering the flue, strip insulation between the bed of insulation and the sheet support surface, strips of shielding material for varying the width of the flue, and an adjustable positioning device.

U.S. Pat. No. 4,677,970 issued on Jul. 7, 1987, to Carlos J. Green et al. describes an orthopedic heat transfer system built into orthopedic casts or splints using a flowing liquid system.

U.S. Pat. No. 5,615,604 issued on Apr. 1, 1997, to Yueh-Kung Chenglin describes a personal cooking appliance comprising a case with two heaters equipped with a timer and a switch.

U.S. Pat. No. 5,782,780 issued on Jul. 21, 1998, to Bradley R. Mason et al. describes a method of forming an contoured orthotic member conforming to a contour of a body by converting a flat pliable member to conform to the body and heat treating to form a stiff member which is covered with a cushioning coating.

U.S. Pat. No. 6,138,662 issued on Oct. 31, 2000, to David M. Jones describes a radiant heater comprising a radiative heating element in a housing having a heat reflective surface.

None of the above inventions and patents, taken either singularly or in combination, is seen to describe the instant invention as claimed. Thus, a heater for orthopedic splints solving the aforementioned problems is desired.

SUMMARY OF THE INVENTION

The present invention is a portable case which is heated to warm the plastic orthopedic sheets for immediate use as splints to conform to the body portion requiring immobilization. The rectangular carrying container resembles a conventional suitcase, but has a bottom compartment containing a heating element with the operating controls mounted on the outside adjacent the handle. When an emergency or need arises, the physician or technician activates the heating elements prior to use. The planar plastic splint sheet is held between the two heating surfaces controlled by a temperature controller to warm both sides at once to minimize heating time. The external operating controls comprises a power-on indicator lamp, a temperature indicator and a lamp to indicate when the heater is operating. An A.C. power input female plug on one side of the case outside permits the connection of an A.C. line power. Thus, the physician or technician can pre-warm the plastic splint sheets prior to application.

Accordingly, it is a principal object of the invention to provide a means for pre-warming plastic sheets.

It is another object of the invention to provide a device to pre-warm plastic splint sheets before application to an injured person's body.

It is a further object of the invention to provide a device that warms the plastic sheets on both sides simultaneously to minimize the heating period.

Still another object of the invention is to provide a device which can adjust the required temperature desired to render the plastic splint sheets pliable for use.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
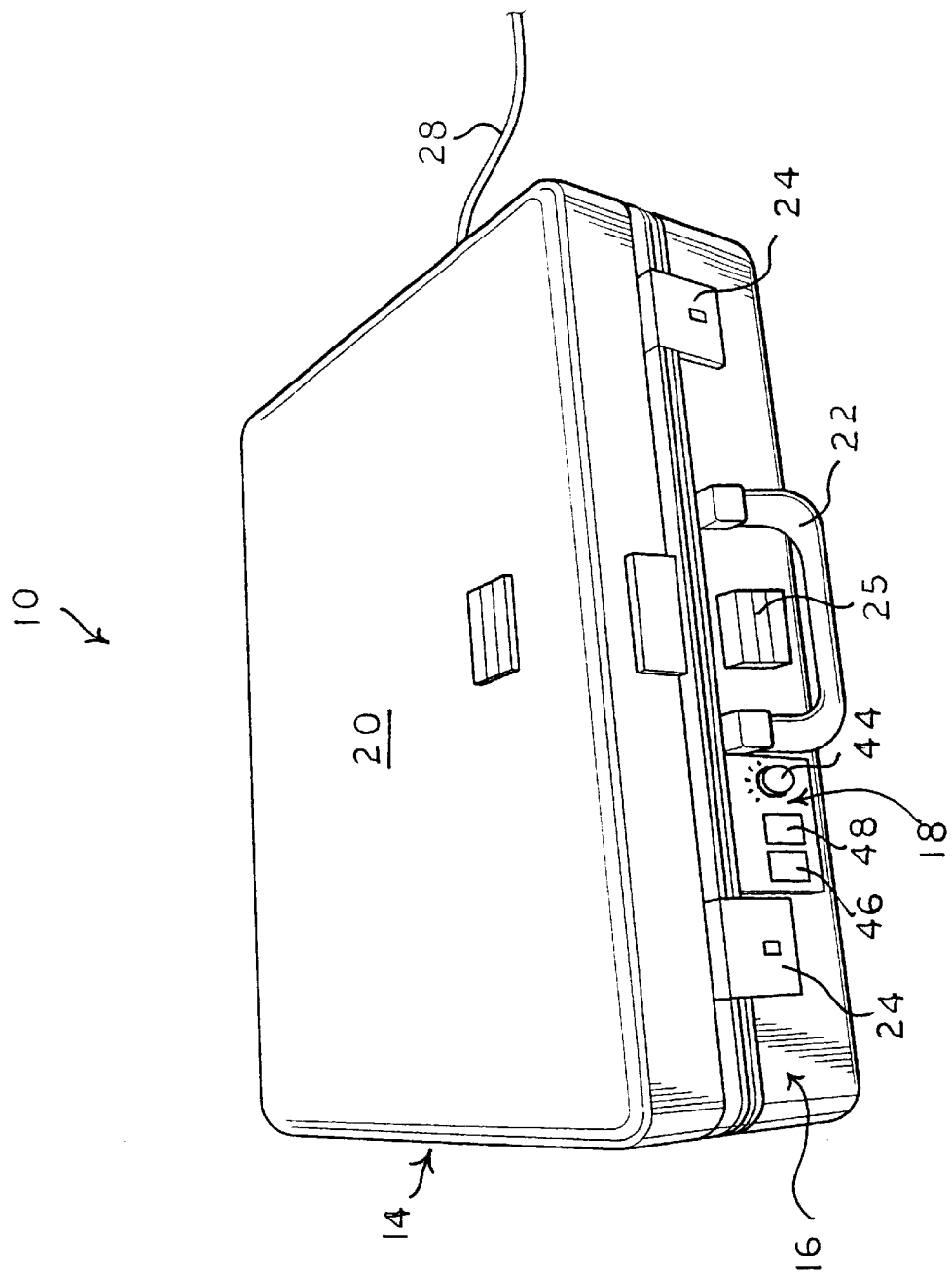
FIG. 1 is an environmental, perspective view of a closed heated container for orthopedic splints according to the present invention.
Figure 2:
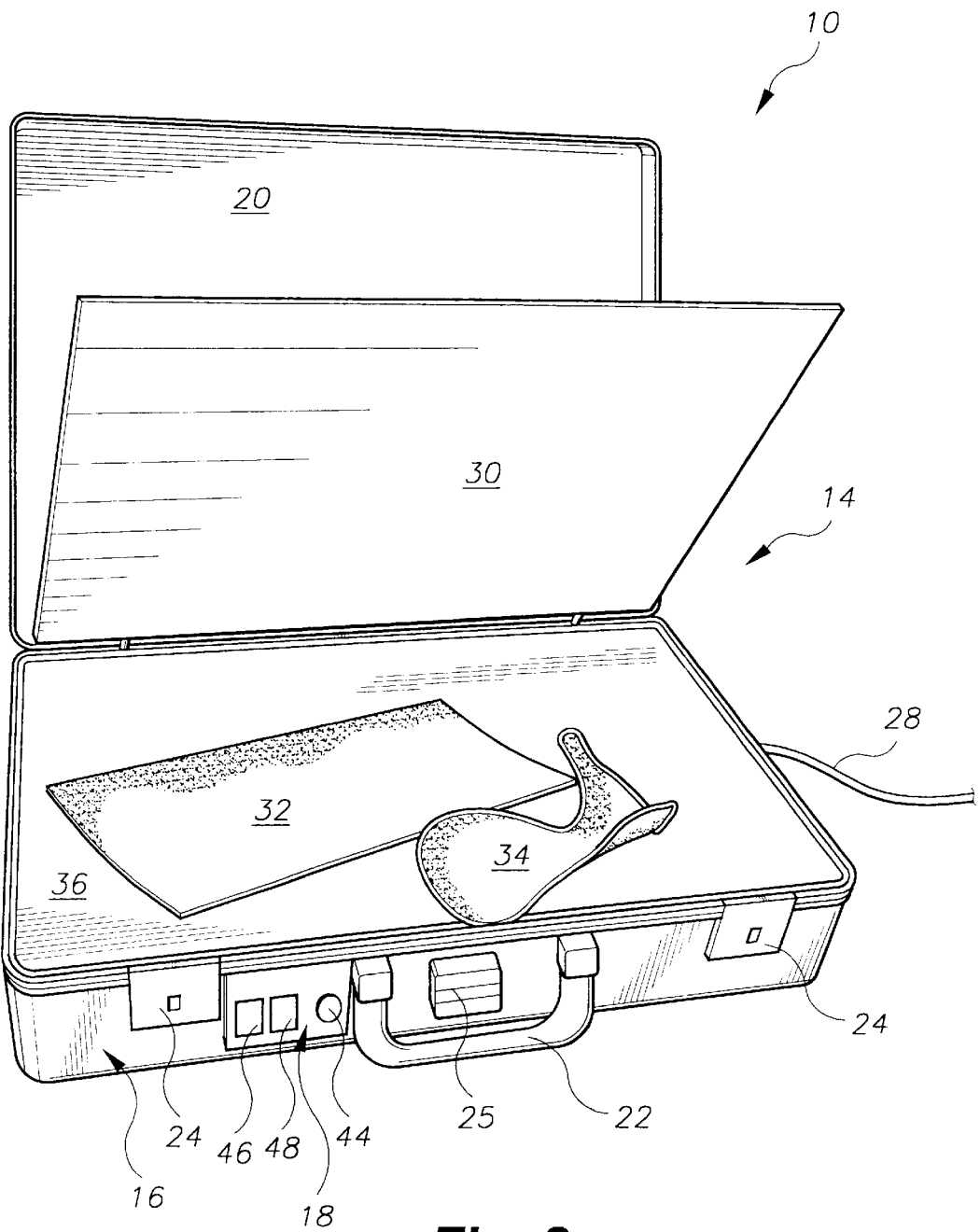
FIG. 2 is a perspective view of the open heated container with two orthopedic splints with one splint pre-formed according to the present invention.

The present invention is directed to a portable heater case 10 illustrated in FIGS. 1 and 2 for preheating orthopedic splints 12 comprising a flat case or container 14 having an outside front side surface 16 with a control panel 18. The container 14 has a hinged lid 20, a pivoting handle 22, a pair of container latches 24, a container lock 25, and an electrical outlet plug or 115 V. A.C. power input 26 (FIG. 3) on one side of the container 14. An electric cord 28 is shown in FIG. 1. The electrical power system will be based on a 110 volt A.C. source.

Figure 3:
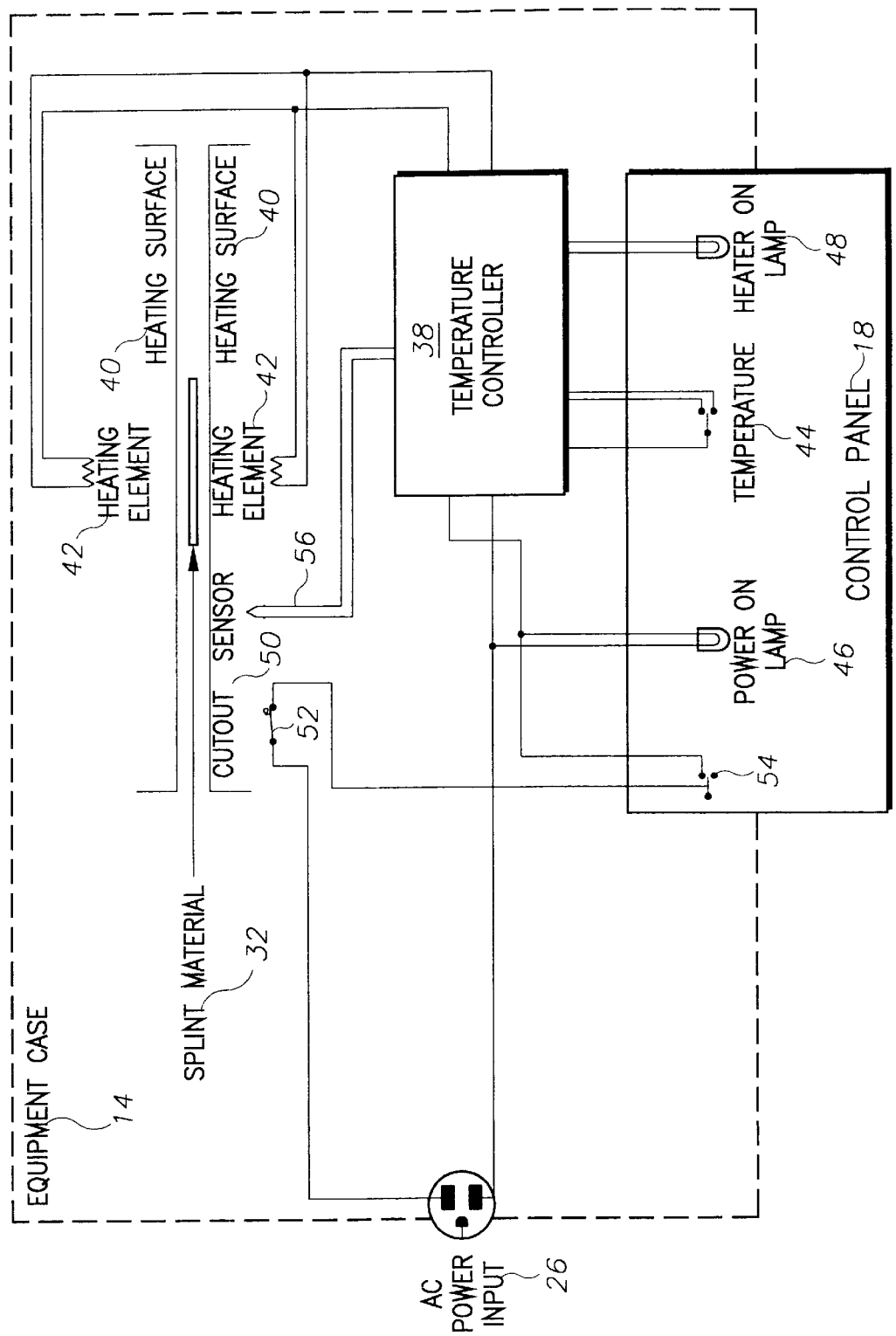
FIG. 3 is a diagram of the electrical system for the container.

FIG. 2 shows a first hinged separator panel 30 with two orthopedic splints, i.e., a flat rectangular splint 32 and a preformed configured splint 34, lying on a second flat rectangular hinged panel 36 which is co-planar with the case's edge for accessing the electrical components shown in FIG. 3.

Inside the heater container 10, as best shown in FIG. 3, a temperature controller element 38 which is computerized with a microcomputer controls the heating temperature and heating period of the two parallel heating surfaces or platens 40 inside heated electrically by heating elements 42. The top platen is hinged (not shown) in a manner to the bottom platen that when the case 14 is closed, the platens are parallel one another and in contact. The hinge also permits the splint material to be tightly held by the parallel platens 40. The splint material 32 is inserted between the metal platens or heating surfaces 40, and the variable temperature setting knob with a temperature scale settings 44 on the outside control panel 18.

Alternatively, a toggle switch with predetermined temperature settings can be substituted. When the heating temperature for the specific splint material 32 is set by knob 44 or the toggle switch, the electric power from the connected electric outlet plug 26 and electric cord 28 activates the "power on" lamp or light emitting diode (LED) 46 and the "heater on" lamp or LED 48 visible on the control panel 18. Normally, several minutes will be all that is required to preheat the orthopedic splints 12.

A cutout sensor element 50 having a thermistor or thermocouple 52 with a preset limiting temperature setting is positioned adjacent the heating element 42, and connected by wire to the AC power input 26 in series with a normally on switch 54 in the control panel 18, and to the temperature controller element 38. The cutoff signal 56 is sent to the thermostat 52 by the programmed temperature controller 38 to initiate the cutout power sequence. Thus, the "power on" lamp 46 and the "heater on" lamp 48 will be turned off by the temperature controller element 38 as well. It should be noted that the power source is not limited to 115 V.A.C. or 60 Hertz in the U.S., but can be made suitable for other electrical systems such as 50, 100, 220, or 240 Hertz.

Heat formable plastic or thermoplastic material is widely used for occupational therapy and orthopedic splints. Johnson and Johnson ORTHOPLAST (TM), inter alia, is one example of such a material. The splinting material is preferably heated at either of three preset temperatures, i.e., approximately 170° F. (high), 160° F. (medium), and 140° F. (low) to make it pliable due to different sizes or composition of the thermoplastic material utilized. Thus, the rotary dial 44 or toggle switch would have three settings. After heating, the material is cut to size and formed to the required shape. Upon cooling, the material still retains its formed shape.

Hot water baths are commonly used for heating this material, but the baths are relatively expensive, not readily portable, and potentially hazardous. The present invention has the advantages of heating the splinting material quickly, safely, and conveniently. The invention is intended for use in occupational therapy, orthopedic hospital areas, doctor's office, emergency medical treatment areas, playing fields for sports injuries, and any location where physical injuries are likely to occur and immediate, temporary immobilization of the injured appendage for safety is important.

Thus, a planar plastic orthopedic splint sheet can be pre-warmed for use between the two parallel heating elements while en route to or at the scene of an accident saving precious time.

It is to be understood that the present invention is not limited to the embodiment described above, but encompasses any and all embodiments within the scope of the following claims.

We claim:

1. A heating container for orthopedic splints comprising:
    a flat container having an outside front side surface;
    a control panel located on said outside side surface;
    a temperature controller element inside the container;
    two parallel planar heating elements or platens positioned inside the container; and
    a first panel separator hinged inside the container to cover the temperature controller element and the two parallel planar heating elements;
    whereby a planar plastic orthopedic splint sheet can be pre-warmed between the two parallel heating elements to form the planar plastic sheet into a desired shape for use as an orthopedic splint.

2. The heater container according to claim 1, wherein an A.C. power input plug is located on one side of the container.

3. The heater container according to claim 1, wherein the control panel contains a temperature control dial or toggle switch electrically connected to the temperature controller element.

4. The heater container according to claim 3, wherein the temperature control dial or toggle switch has a plurality of preset temperature settings.

5. The heater container according to claim 1, wherein the control panel contains a heater-on indicator lamp electrically connected to the temperature controller element.

6. The heater container according to claim 1, wherein the control panel contains a power-on indicator lamp.

7. The heater container according to claim 6, wherein the power-on indicator lamp is electrically connected in series with the temperature controller element and with an A.C. power input plug located on another side of the heater container.

8. The heater container according to claim 1, wherein a cutout sensor element for stopping the flow of electricity to the heating elements is located adjacent the heating elements.

9. The heater container according to claim 8, wherein the cutout sensor element is wired to the control panel and to an A.C. power input plug located on one side of the container.

10. The heater container according to claim 8, wherein the temperature controller element is wired to the cutout sensor element in the control panel by a normally off switch.

11. The heater container according to claim 1, wherein a second panel separator is hinged inside the container to cover a supply of planar plastic orthopedic splint sheets of different configurations carried for future use.

* * * * *